United States Patent
Wang et al.

(10) Patent No.: US 10,634,917 B2
(45) Date of Patent: Apr. 28, 2020

(54) SMART USER EXPERIENCE APPARATUS AND SMART HELMET

(71) Applicants: BOE TECHNOLOGY GROUP CO., LTD., Beijing (CN); ORDOS YUANSHENG OPTOELECTRONICS CO., LTD., Inner Mongolia (CN)

(72) Inventors: Ning Wang, Beijing (CN); Lei Ding, Beijing (CN); Pan Guo, Beijing (CN); Wei Li, Beijing (CN); Yanqing Chen, Beijing (CN)

(73) Assignees: BOE TECHNOLOGY GROUP CO., LTD., Beijing (CN); ORDOS YUANSHENG OPTOELECTRONICS CO., LTD., Inner Mongolia (CN)

( * ) Notice: Subject to any disclaimer, the term of this patent is extended or adjusted under 35 U.S.C. 154(b) by 119 days.

(21) Appl. No.: 15/755,674

(22) PCT Filed: Sep. 15, 2017

(86) PCT No.: PCT/CN2017/101822
§ 371 (c)(1),
(2) Date: Feb. 27, 2018

(87) PCT Pub. No.: WO2018/145460
PCT Pub. Date: Aug. 16, 2018

(65) Prior Publication Data
US 2019/0025591 A1 Jan. 24, 2019

(30) Foreign Application Priority Data
Feb. 10, 2017 (CN) .................... 2017 2 0127665 U

(51) Int. Cl.
*G02B 27/01* (2006.01)
*G02B 13/00* (2006.01)
(Continued)

(52) U.S. Cl.
CPC ....... *G02B 27/0172* (2013.01); *G02B 13/003* (2013.01); *G02B 27/0093* (2013.01);
(Continued)

(58) Field of Classification Search
CPC .............. G02B 27/0172; G02B 13/003; G02B 2027/0138; G02B 2027/014; A61B 3/028
See application file for complete search history.

(56) References Cited

U.S. PATENT DOCUMENTS

| 2013/0329305 | A1* | 12/2013 | Kunugise | ............ G02B 15/177 359/691 |
| 2014/0049683 | A1* | 2/2014 | Guenter | ................ H04N 5/262 348/360 |
| 2015/0138048 | A1 | 5/2015 | Park | |

FOREIGN PATENT DOCUMENTS

| CN | 105653227 | 6/2016 |
| CN | 106125310 | 11/2016 |

(Continued)

OTHER PUBLICATIONS

International Searching Authority, "International Search Report and Written Opinion," issued in connection with International Patent Application No. PCT/CN2017/101822, dated Dec. 19, 2017, 12 pages.

(Continued)

*Primary Examiner* — Wing H Chow
(74) *Attorney, Agent, or Firm* — Arent Fox LLP; Michael Fainberg

(57) ABSTRACT

The application discloses a smart user experience apparatus and a smart helmet, and the smart user experience apparatus
(Continued)

includes a display device and a watching device, and further includes: a detecting device, located on the side of the watching device facing the experiencing user, configured to detect diopters of eyes of an experiencing user; and a vision correction device, located on the side of the watching device facing the experiencing user, connected with the detecting device, and configured to compensate for the vision of the experiencing user according to the diopters detected by the detecting device, so visions of experiencing users with the different visions can be compensated differently for, so that a nearsighted or farsighted experiencing user can see a clear image during watching even without wearing his or her glasses, thus eliminating his or her feeling of a pressure on his or her eyes while the experiencing user is wearing his or her glasses as in the prior art.

8 Claims, 2 Drawing Sheets

(51) Int. Cl.
*A61B 3/028* (2006.01)
*G02B 27/00* (2006.01)

(52) U.S. Cl.
CPC ........ *A61B 3/028* (2013.01); *G02B 2027/014* (2013.01); *G02B 2027/0134* (2013.01); *G02B 2027/0138* (2013.01)

(56) References Cited

FOREIGN PATENT DOCUMENTS

| | | |
|---|---|---|
| CN | 106291931 | 1/2017 |
| CN | 106291938 | 1/2017 |
| CN | 106444028 | 2/2017 |

OTHER PUBLICATIONS

State Intellectual Property Office of People's Republic of China, "Notification of the First Office Action," issued in connection with Chinese Patent Application No. 201720127665.8, dated Jul. 24, 2017, 3 pages.

\* cited by examiner

SMART USER EXPERIENCE APPARATUS AND SMART HELMET

This application is a US National Stage of International Application No. PCT/CN2017/101822, filed on Sep. 15, 2017, designating the United States, and claiming the benefit of Chinese Patent Application No. 201720127665.8, filed with the Chinese Patent Office on Feb. 10, 2017 and entitled "A smart user experience apparatus and a smart helmet", which is hereby incorporated by reference in its entirety.

FIELD

The present application relates to the field of user experience technologies, and particularly to a smart user experience apparatus and a smart helmet.

BACKGROUND

Augmented reality (AR) (VR) is a new display mode further to a 3D display mode, which is used to enhance a human-environment interaction experience. A sensor loaded in an AR helmet can detect and track a moving head and eyes of a user constantly, and track user data, so that virtual information can be overlaid on the real word, by simulating and integrating physical information, which would otherwise be difficult to experience for some time and in some space, into the real world.

However, the existing AR helmet in use may be unfriendly to nearsighted or farsighted users in that an experiencing user has to wear his or her glasses due to his or her problematic vision, so that his or her eyes are pressed for a long period of time, thus seriously degrading his or her experience.

SUMMARY

An embodiment of the application provides a smart user experience apparatus including a display device and a watching device, where the display device is configured to provide the watching device with virtual information, and the watching device is configured to present the received virtual information to an experiencing user, or to integrate the received virtual information with reality information, and then present the integrated information to the experiencing user; and the smart user experience apparatus further includes:

a detecting device, located on a side of the watching device facing the experiencing user, configured to detect diopters of eyes of the experiencing user; and a vision correction device, located on the side of the watching device facing the experiencing user, connected with the detecting device, and configured to compensate for the vision of the experiencing user according to the diopters detected by the detecting device.

In the smart user experience apparatus according to the embodiment of the application, the detecting device includes:

a sensor configured to transmit a light wave to the eyes of the experiencing user, and to receive a light wave reflected back from the eyes; and a first computing processor connected with the sensor, and configured to calculate the diopters of the eyes of the experiencing user according to the light wave transmitted, and the light wave received, by the sensor.

In the smart user experience apparatus according to the embodiment of the application, the detecting device includes:

an image source configured to provide the eyes of the experiencing user with a test image;

a set of lenses, located on the side of the image source facing the experiencing user, composed of a plurality of lenses with their light axes coincide with each other, where the test image provided by the image source arrives at the eyes of the experiencing user through the set of lenses;

an image detecting device configured to detect an extent of clarity of the test image imaged onto retinas of the experiencing user;

a lens adjusting device configured to adjust distances between the respective lenses in the set of lenses, and the retinas of the experiencing user according to the extent of clarity detected by the image detecting device; and a first computing processor configured to calculate the diopters of the eyes of the experiencing user according to the distances between the respective lenses in the set of lenses, and the retinas of the experiencing user when the extent of clarity detected by the image detecting device is satisfactory.

In the smart user experience apparatus according to the embodiment of the application, the set of lenses includes a plurality of concave lenses, and a plurality of convex lenses.

In the smart user experience apparatus according to the embodiment of the application, at least a part of the concave lenses have different focal lengths.

In the smart user experience apparatus according to the embodiment of the application, at least a part of the convex lenses have different focal lengths.

In the smart user experience apparatus according to the embodiment of the application, the vision correction device includes the lens adjusting device and the set of lenses.

In the smart user experience apparatus according to the embodiment of the application, the image source is a same device as the watching device.

In the smart user experience apparatus according to the embodiment of the application, the vision correction device includes:

a lens structure;

a second computing processor connected with the detecting device, and configured to determine a curvature radius of the lens structure according to the diopters detected by the detecting device; and a lens adjusting device connected with the second computing processor, and configured to adjust the curvature radius of the lens structure according to the curvature radius determined by the second computing processor.

An embodiment of the application further provides a smart helmet including a helmet body, and the smart user experience apparatus above according to any one of the embodiments above, where at least the watching device, the detecting device, and the vision correction device of the smart user experience apparatus are arranged on the body.

DETAILED DESCRIPTION OF THE EMBODIMENTS

Figure 1:
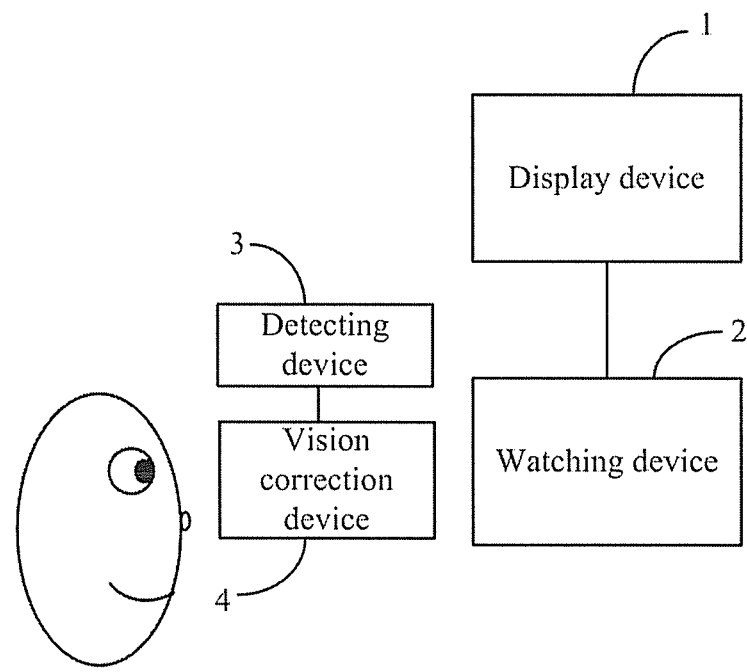
FIG. 1 is a schematic structural diagram of a smart experience device according to an embodiment of the application.

In order to make the objects, technical solutions, and advantages of the application more apparent, the application will be described below in further details with reference to the drawings. Apparently the embodiments to be described below are only a part but not all of the embodiments of the application. Based upon the embodiments of this disclosure here, all of other embodiments which can occur to those ordinarily skilled in the art without any inventive effort shall come into the scope of the application as claimed.

The shapes and sizes of respective components in the drawings are not intended to reflect any real proportion, but merely intended to illustrate the disclosure of the application.

As illustrated in FIG. 1, a smart user experience apparatus according to an embodiment of the application includes a display device 1 and a watching device 2, where the display device 1 is configured to provide the watching device 2 with virtual information, and the watching device 2 is configured to present the received virtual information to an experiencing user, or to integrate the received virtual information with reality information, and then present the integrated information to the experiencing user; and the smart user experience apparatus further includes:

a detecting device 3, located on the side of the watching device 2 facing the experiencing user, configured to detect the diopters of eyes of the experiencing user; and a vision correction device 4, located on the side of the watching device 2 facing the experiencing user, connected with the detecting device 3, and configured to compensate for the vision of the experiencing user according to the diopters detected by the detecting device 3.

Particularly in the smart user experience apparatus above according to the embodiment of the application, the diopters of the eyes of the experiencing user can be detected by the detecting device 3 located on the side of the watching device 2 facing the experiencing user, and thereafter the vision of the experiencing user can be compensated for by the vision correction device 4 located on the side of the watching device 2 facing the experiencing user according to the diopters detected by the detecting device 3, so the visions of experiencing users with the different visions can be compensated differently for, so that a nearsighted or farsighted experiencing user can see a clear image during watching even without wearing his or her glasses, thus eliminating his or her feeling of a pressure on his or her eyes while the experiencing user is wearing his or her glasses as in the prior art.

Optionally when the smart user experience apparatus above according to the embodiment of the application is virtual reality experience apparatus, the watching device 2 can be configured to present the received virtual information to the experiencing user; and when the smart user experience apparatus above according to the embodiment of the application is an augmented reality experience apparatus, the watching device 2 can be configured to integrate the received virtual information with the reality information, and then present the integrated information to the experiencing user.

Optionally in the smart user experience apparatus above according to the embodiment of the application, the display device 1 can be a computer, a TV set, or another device with a display function, and accordingly the watching device 2 can be smart glasses or the like, although the embodiment of the application will not be limited thereto.

Optionally in the smart user experience apparatus above according to the embodiment of the application, the display device 1 and the watching device 2 can be the same as counterparts in the existing augmented reality experience apparatus or virtual reality experience apparatus, although a repeated description thereof will be omitted here.

Optionally in the smart user experience apparatus above according to the embodiment of the application, the detecting device 3 can be a device configured to detect the diopters of human eyes using reflected light, e.g., a sensor. The detecting device 3 can alternatively be a device configured to detect the diopters of human eyes under such a principle that a lens images an object clearly onto retinas, and for example, the detecting device 3 can be an optometry apparatus in an optical shop, although the embodiment of the application will not be limited thereto.

Figure 2:
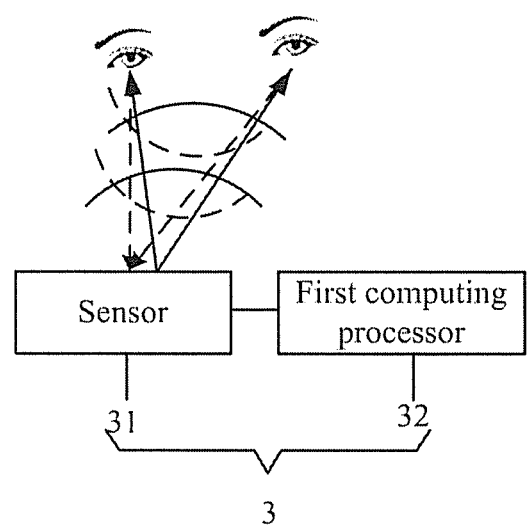
FIG. 2 is a first schematic structural diagram of a detecting device in the smart experience device according to the embodiment of the application.

Optionally in the smart user experience apparatus above according to the embodiment of the application, as illustrated in FIG. 2, the detecting device 3 can include:

a sensor 31 configured to transmit a light wave to the eyes of the experiencing user, and to receive a light wave reflected back from the eyes; and a first computing processor 32 connected with the sensor 31, and configured to calculate the diopters of the eyes of the experiencing user according to the light wave transmitted, and the light wave received, by the sensor 31.

Optionally in the smart user experience apparatus above according to the embodiment of the application, the first computing processor 32 can be integrated on the sensor 31 to thereby facilitate the integrity and minimization of the detecting device 3.

Figure 3:
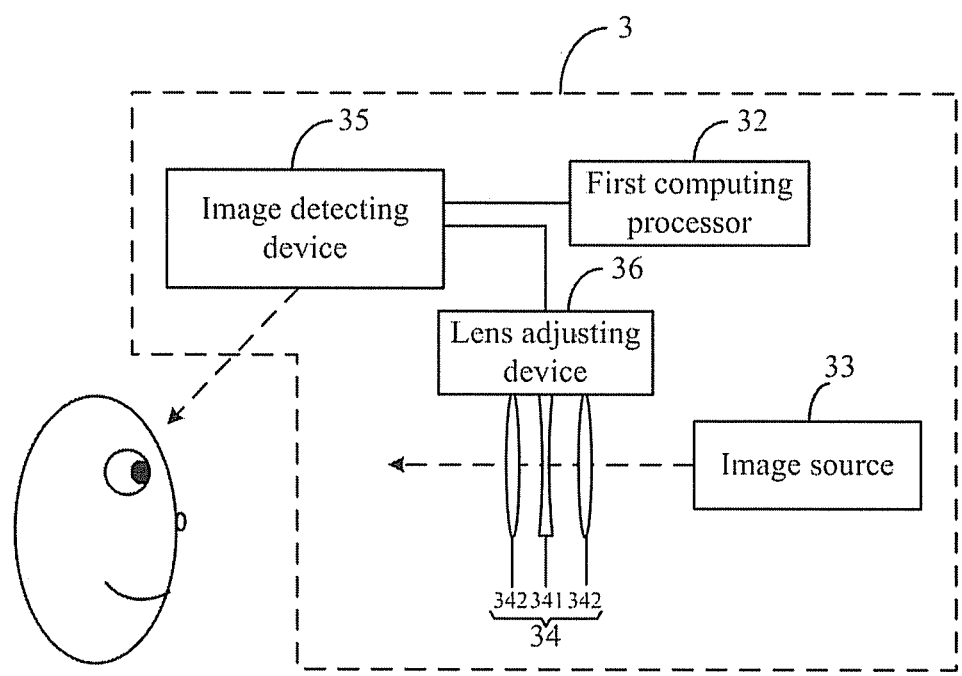
FIG. 3 is a second schematic structural diagram of the detecting device in the smart experience device according to the embodiment of the application.

Optionally in the smart user experience apparatus above according to the embodiment of the application, as illustrated in FIG. 3, the detecting device 3 can further include:

an image source 33 configured to provide the eyes of the experiencing user with a test image;

a set of lenses 34, located on the side of the image source 33 facing the experiencing user, composed of a plurality of lenses 341 and 342 with their optic axes coincide with each other, where the test image provided by the image source 33 arrives at the eyes of the experiencing user through the set of lenses 34;

an image detecting device 35 configured to detect the extent of clarity of the test image being imaged onto the retinas of the experiencing user;

a lens adjusting device 36 configured to adjust the distances between the respective lenses 341 and 342 in the set of lenses 34, and the retinas of the experiencing user according to the extent of clarity detected by the image detecting device 35; and a first computing processor 32 configured to calculate the diopters of the eyes of the experiencing user according to the distances between the respective lenses 341 and 342 in the set of lenses 34, and the retinas of the experiencing user when the extent of clarity detected by the image detecting device 35 is satisfactory.

Optionally in the smart user experience apparatus above according to the embodiment of the application, the watching device 2 can be reused as the image source 33, that is, the image source 33 can be the same device as the watching device 2, thus reducing the number of devices in the smart user experience apparatus, and improving the integrity of the devices.

Optionally in the smart user experience apparatus above according to the embodiment of the application, the set of lenses 34 can include a plurality of concave lenses 341, and a plurality of convex lenses 342 as illustrated in FIG. 3. The lens adjusting device 36 can adjust the distances between the respective lenses 341 and 342 in the set of lenses 34, and the retinas of the experiencing user to thereby adjust the degree of the set of lenses 34 functioning as glasses.

Optionally in the smart user experience apparatus above according to the embodiment of the application, at least a part of the concave lenses 341 in the set of lenses 34 may have different focal lengths to thereby facilitate a larger detection range.

Optionally in the smart user experience apparatus above according to the embodiment of the application, at least a part of the convex lenses 342 in the set of lenses 34 may have different focal lengths to thereby facilitate a larger detection range.

Optionally the larger the number of concave lenses 341 and convex lenses 342 with different focal lengths included in the set of lenses 34 is, the range of degrees of glasses available from the set of lenses 34 becomes larger.

Optionally in the smart user experience apparatus above according to the embodiment of the application, the vision correction device 4 compensates for the vision under the same principle as glasses in that the diopters of flexible lenses are adjusted according to varying curvature of the lenses so that an object can be seen clearly by human eyes. Accordingly the vision correction device 4 can be composed of flexible lenses, and a device for adjusting the diopters of the flexible lenses, although the embodiment of the application will not be limited thereto.

Figure 4:
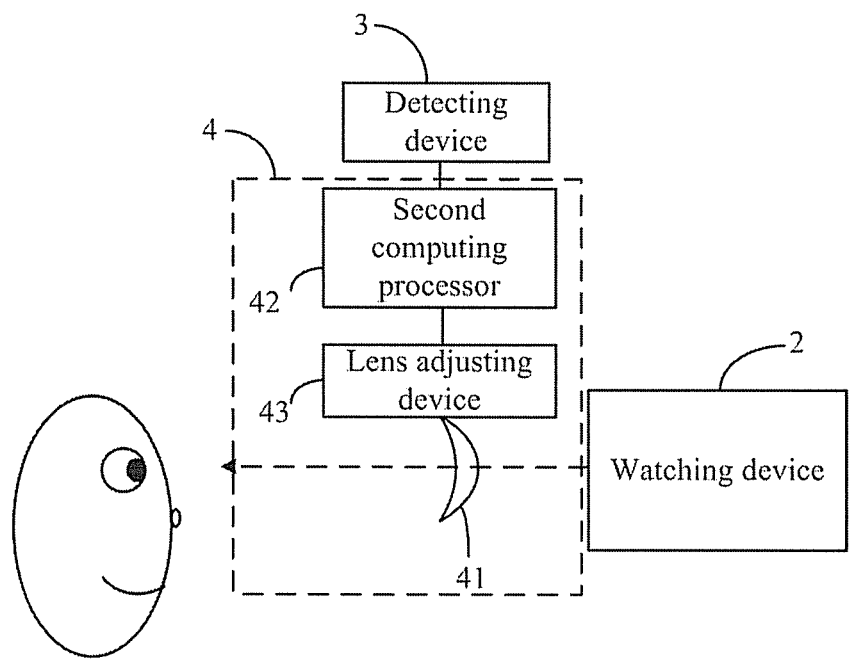
FIG. 4 is a schematic structural diagram of a vision correction device in the smart experience device according to the embodiment of the application.

Optionally in the smart user experience apparatus above according to the embodiment of the application, as illustrated in FIG. 4, the vision correction device 4 can include:

a lens structure 41;

a second computing processor 42 connected with the detecting device 3, and configured to determine a curvature radius of the lens structure 41 according to the diopters detected by the detecting device 3; and a lens adjusting device 43 connected with the second computing processor 42, and configured to adjust the curvature radius of the lens structure 41 according to the curvature radius determined by the second computing processor 42.

Particularly human eyes are nearsighted or farsighted because parallel light rays passing lenses of the eyes are not converged onto the retinas, so the lens structure 41 can be equivalent to lenses. The curvature radius of the lens structure 41 is adjusted according to the diopters of different eyes so that the lenses of the eyes match the lens structure 41, and in this way, an image of the watching device 2 can be imaged clearly onto the retinas of the experiencing user, that is, the image of the watching device 2 can be seen clearly by the experiencing user.

Optionally the first computing processor 32 and the second computing processor 42 can be Field Programmable Gate Arrays (FPGAs), Complex Programmable Logic Devices (CPLDs), Acorn RISC Machines (ARMs), processors, Programmable Logic Controllers (PLCs), etc., although the embodiment of the application will not be limited thereto.

Based upon the same inventive idea, an embodiment of the application further provides a smart helmet including a helmet body, and the smart user experience apparatus above according to any one of the embodiments of the application, where at least the watching device, the detecting device, and the vision correction device of the smart user experience apparatus are arranged on the body. Since the smart helmet addresses the problem under a similar principle to the smart user experience apparatus above, reference can be made to the implementation of the smart user experience apparatus above for an implementation of the smart helmet, although a repeated description thereof will be omitted here.

In the smart user experience apparatus and the smart helmet according to the embodiments of the application, the diopters of the eyes of the experiencing user can be detected by the detecting device located on the side of the watching device facing the experiencing user, and thereafter the vision of the experiencing user can be compensated for by the vision correction device located on the side of the watching device facing the experiencing user according to the diopters detected by the detecting device, so the visions of experiencing users with the different visions can be compensated differently for, so that a nearsighted or farsighted experiencing user can see a clear image during watching even without wearing his or her glasses, thus eliminating his or her feeling of a pressure on his or her eyes while the experiencing user is wearing his or her glasses as in the prior art.

Those skilled in the art shall appreciate that the embodiments of the application can be embodied as a method, a system or a computer program product. Therefore the application can be embodied in the form of an all-hardware embodiment, an all-software embodiment or an embodiment of software and hardware in combination. Furthermore the application can be embodied in the form of a computer program product embodied in one or more computer useable storage mediums (including but not limited to a disk memory, a CD-ROM, an optical memory, etc.) in which computer useable program codes are contained.

The application has been described in a flow chart and/or a block diagram of the method, the device (system) and the computer program product according to the embodiments of the application. It shall be appreciated that respective flows and/or blocks in the flow chart and/or the block diagram and combinations of the flows and/or the blocks in the flow chart and/or the block diagram can be embodied in computer program instructions. These computer program instructions can be loaded onto a general-purpose computer, a specific-purpose computer, an embedded processor or a processor of another programmable data processing device to produce a machine so that the instructions executed on the computer or the processor of the other programmable data processing device create means for performing the functions specified in the flow(s) of the flow chart and/or the block(s) of the block diagram.

These computer program instructions can also be stored into a computer readable memory capable of directing the computer or the other programmable data processing device to operate in a specific manner so that the instructions stored in the computer readable memory create an article of manufacture including instruction means which perform the functions specified in the flow(s) of the flow chart and/or the block(s) of the block diagram.

These computer program instructions can also be loaded onto the computer or the other programmable data processing device so that a series of operational steps are performed on the computer or the other programmable data processing device to create a computer implemented process so that the instructions executed on the computer or the other programmable device provide steps for performing the functions specified in the flow(s) of the flow chart and/or the block(s) of the block diagram.

Although the preferred embodiments of the application have been described, those skilled in the art benefiting from the underlying inventive concept can make additional modifications and variations to these embodiments. Therefore the appended claims are intended to be construed as encompassing the preferred embodiments and all the modifications and variations coming into the scope of the application.

Evidently those skilled in the art can make various modifications and variations to the application without departing from the spirit and scope of the application. Thus the application is also intended to encompass these modifications and variations thereto so long as the modifications and variations come into the scope of the claims appended to the application and their equivalents.

The invention claimed is:

1. A smart user experience apparatus, comprising a display device and a watching device, wherein the display device is configured to provide the watching device with virtual information, and the watching device is configured to present the received virtual information to an experiencing user, or to integrate the received virtual information with reality information, and then present the integrated information to the experiencing user; and the smart user experience apparatus further comprises:
   a detecting device, located on a side of the watching device facing the experiencing user, configured to detect diopters of eyes of the experiencing user; and
   a vision correction device, located on the side of the watching device facing the experiencing user, connected with the detecting device, and configured to compensate for vision of the experiencing user according to the diopters detected by the detecting device;
   wherein the detecting device further comprises:
      an image source configured to provide the eyes of the experiencing user with a test image, wherein the test image is used to detect the diopters of eyes of the experiencing user;
      a set of lenses, located on a side of the image source facing the experiencing user, composed of a plurality of lenses with their light axes coincide with each other, wherein the test image provided by the image source arrives at the eyes of the experiencing user through the set of lenses;
      an image detecting device configured to detect an extent of clarity of the test image imaged onto retinas of the experiencing user;
      a lens adjusting device configured to adjust distances between the retinas of the experiencing user, and the respective lenses in the set of lenses according to the extent of clarity detected by the image detecting device; and
      a first computing processor configured to calculate the diopters of the eyes of the experiencing user according to the distances between the retinas of the experiencing user, and the respective lenses in the set of lenses when the extent of clarity detected by the image detecting device is satisfactory;
   wherein the vision correction device comprises:
      a lens structure;
      a second computing processor connected with the detecting device, and configured to determine a curvature radius of the lens structure according to the diopters of the eyes of the experiencing user detected by the detecting device; and
      a lens structure adjusting device connected with the second computing processor, and configured to adjust the curvature radius of the lens structure according to the curvature radius determined by the second computing processor.

2. The smart user experience apparatus according to claim 1, wherein the set of lenses in the detecting device comprises a plurality of concave lenses, and a plurality of convex lenses.

3. The smart user experience apparatus according to claim 2, wherein at least a part of the concave lenses have different focal lengths.

4. The smart user experience apparatus according to claim 3, wherein the image source is a same device as the watching device.

5. The smart user experience apparatus according to claim 2, wherein at least a part of the convex lenses have different focal lengths.

6. The smart user experience apparatus according to claim 5, wherein the image source is a same device as the watching device.

7. The smart user experience apparatus according to claim 1, wherein the image source is a same device as the watching device.

8. A smart helmet, comprising a helmet body, and the smart user experience apparatus above according to claim 1, wherein at least the watching device, the detecting device, and the vision correction device of the smart user experience apparatus are arranged on the body;
   wherein the detecting device further comprises:
      an image source configured to provide the eyes of the experiencing user with a test image, wherein the test image is used to detect the diopters of eyes of the experiencing user;
      a set of lenses, located on a side of the image source facing the experiencing user, composed of a plurality of lenses with their light axes coincide with each other, wherein the test image provided by the image source arrives at the eyes of the experiencing user through the set of lenses;
      an image detecting device configured to detect an extent of clarity of the test image imaged onto retinas of the experiencing user;
      a lens adjusting device configured to adjust distances between the retinas of the experiencing user, and the respective lenses in the set of lenses according to the extent of clarity detected by the image detecting device; and
      a first computing processor configured to calculate the diopters of the eyes of the experiencing user according to the distances between the retinas of the experiencing user, and the respective lenses in the set of lenses when the extent of clarity detected by the image detecting device is satisfactory;
   wherein the vision correction device comprises:
      a lens structure;
      a second computing processor connected with the detecting device, and configured to determine a curvature radius of the lens structure according to the diopters of the eyes of the experiencing user detected by the detecting device; and
      a lens structure adjusting device connected with the second computing processor, and configured to adjust the curvature radius of the lens structure according to the curvature radius determined by the second computing processor.

* * * * *